United States Patent
Kim

(10) Patent No.: US 9,931,217 B2
(45) Date of Patent: Apr. 3, 2018

(54) TWO-PART ARTICULATING JOINT SPACER AND METHOD FOR PRODUCING SAID JOINT SPACER

(71) Applicant: Heraeus Medical GmbH, Wehrheim (DE)

(72) Inventor: Hieng Kim, Nidderau (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 436 days.

(21) Appl. No.: 14/321,241

(22) Filed: Jul. 1, 2014

(65) Prior Publication Data
US 2015/0012105 A1   Jan. 8, 2015

(30) Foreign Application Priority Data

Jul. 8, 2013   (DE) ........................ 10 2013 011 296

(51) Int. Cl.
*A61F 2/38*   (2006.01)
*A61F 2/30*   (2006.01)

(52) U.S. Cl.
CPC ........ *A61F 2/3872* (2013.01); *A61F 2/30965* (2013.01); *A61F 2/38* (2013.01);
(Continued)

(58) Field of Classification Search
CPC ......... A61F 2/38; A61F 2/3868; A61F 2/3872
(Continued)

(56) References Cited

U.S. PATENT DOCUMENTS 5,123,927 A * 6/1992 Duncan ............... A61F 2/30942
                                                                  623/20.21
6,155,812 A   12/2000 Smith et al.
(Continued)

FOREIGN PATENT DOCUMENTS

CA      2618408 A1    7/2008
CN    101229391 A     7/2008
(Continued)

OTHER PUBLICATIONS

English translation of JP Notification of Reasons for Refusal for Japanese patent application 2014-140361 dated May 25, 2015.
(Continued)

*Primary Examiner* — David Isabella
*Assistant Examiner* — Christine Nelson
(74) *Attorney, Agent, or Firm* — Norris McLaughlin & Marcus PA

(57) ABSTRACT

The invention relates to an articulating joint spacer for temporary replacement of a joint, whereby the joint spacer comprises two spacer parts which each comprise one sliding surface on which the spacer parts, in the patient-inserted state, touch against each other in mobile manner and roll off on each other, and the remaining spacer parts are made, at least in part, of a second bone cement that contains at least one water-soluble antibiotic. The invention also relates to a method for producing a two-part articulating joint spacer, in which a sliding surface is formed in both spacer parts from a low-abrasion first bone cement and at least the surfaces of the remaining spacer parts, at least 50% thereof, are formed with a second bone cement that contains at least one water-soluble antibiotic.

15 Claims, 1 Drawing Sheet

(52) U.S. Cl.
CPC ............... *A61F 2002/30016* (2013.01); *A61F 2002/30672* (2013.01); *A61F 2002/30677* (2013.01); *A61F 2310/00353* (2013.01)

(58) Field of Classification Search
USPC ...................................................... 623/20.28
See application file for complete search history.

(56) References Cited

U.S. PATENT DOCUMENTS

| | | | |
|---|---|---|---|
| 6,361,731 | B1 | 3/2002 | Smith et al. |
| 7,842,095 | B2 | 11/2010 | Klein |
| 2005/0107885 | A1* | 5/2005 | Evans ................ A61F 2/30942 623/20.21 |
| 2008/0213336 | A1 | 9/2008 | Kuhn et al. |
| 2008/0269909 | A1* | 10/2008 | Vogt ...................... A61L 24/001 623/23.62 |
| 2010/0042214 | A1 | 2/2010 | Nebosky et al. |
| 2010/0185298 | A1 | 7/2010 | Stone |
| 2011/0015754 | A1* | 1/2011 | Leonard .............. A61F 2/30771 623/22.42 |
| 2012/0261546 | A1 | 10/2012 | Hawkins et al. |

FOREIGN PATENT DOCUMENTS

| | | |
|---|---|---|
| CN | 202821725 U | 3/2013 |
| CN | 103027767 A | 4/2013 |
| EP | 1274374 A1 | 1/2003 |
| JP | 2008264556 A | 11/2008 |
| WO | 01/76512 A1 | 10/2001 |
| WO | 2011086788 A1 | 7/2011 |

OTHER PUBLICATIONS

English Translation of Chinese Office Action dated Nov. 2, 2015 for corresponding Chinese Application No. 201410320248.6.
Canadian Office Action for related Canadian Patent Application No. 2,855,302 dated Sep. 10, 2015.

* cited by examiner

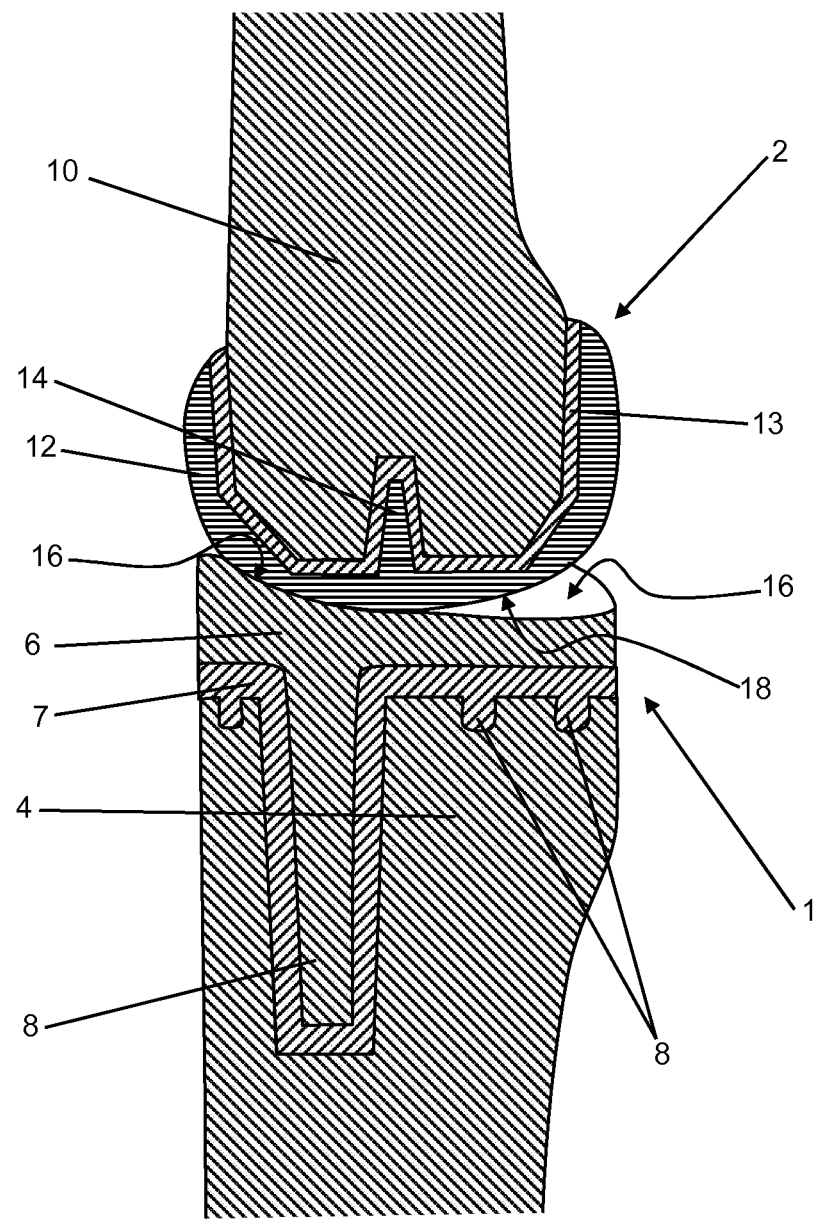

TWO-PART ARTICULATING JOINT SPACER AND METHOD FOR PRODUCING SAID JOINT SPACER

This application claims priority to the German patent application DE 10 2013 011 296.6 filed Jul. 8, 2013.

The invention relates to an articulating joint spacer for temporary replacement of a joint, whereby the joint spacer comprises two spacer parts, which each comprise one sliding surface on which the spacer parts, in the patient-inserted state, touch against each other in mobile manner and roll off on each other. Moreover, the invention relates to a method for producing a two-part articulating joint spacer.

Articular endoprostheses currently have a service life of several years. However, undesirable loosening of the articular endoprostheses can occur before the end of the usual service life. This can concern either septic or aseptic loosening. Aseptic loosening means that no microbial germs are detectable yet. There are many causes of aseptic loosening. Aseptic loosening is often related to abrasion at the sliding surfaces of articular endoprostheses. The loosening process in septic loosening is induced by microbial germs. This can either be early or late infections depending on the time of manifestation. Septic loosening is a very serious disease for the patient and associated with high additional costs. It is customary to perform a revision surgery in cases of aseptic and septic loosening alike. This can proceed as a one-stage or a two-stage revision surgery. Two-stage revision surgeries are very common in cases of septic loosening.

In a two-stage revision surgery, the infected articular endoprosthesis is removed in a first surgery (OP) followed by debridement of the infected tissue and subsequent insertion of a temporary place-holder, a so-called spacer. Said spacer occupies for a number of weeks the space previously occupied by the revised endoprosthesis until the manifest infection has subsided. Said place-holder function is very important in order to effectively prevent muscular atrophy during this period of time and in order to stabilise the existing resection scenario. There are non-articulating and articulating spacers available. Articulating spacers or joint spacers replicate the function of the joint and allow the afflicted limbs to have a certain degree of mobility. This allows the patient to be mobilised early. Articulating spacers are currently the state of the art. The spacer is removed in a second surgery, another debridement is done before implanting a cemented or cement-free revision articular endoprosthesis.

Spacers equipped with antibiotics for temporary replacement of knee, hip, and shoulder endoprostheses are available on the market. Said spacers are known, for example from US 2010/042214 A1 and US 2011/015754 A1. The spacers described therein contain hollow spaces from which the antibiotics are released. The uneven release of the agent is disadvantageous. Alternatively, for example DE 10 2007 004 968 B4 and WO 2011 086788 A1 proposed bone cements from which antibiotics can be eluted by dissolution. Using said bone cements for producing a spacer, the antibiotics are released right at the site of infection over an extended period of time and it must therefore be possible to elute them out of the spacer material by dissolution. A spacer of this type made of bone cement is proposed, for example, in patent application US 2012/0261546 A1.

Spacers are often produced by the surgeon from conventional polymethylmethacrylate bone cements (PMMA bone cements) and suitable casting moulds. In this process, one or more antibiotics are admixed to the PMMA bone cement powder before the spacer is produced. In addition, zirconium oxide powder can be introduced or applied as a radiopaquer to serve as contrast agent for X-ray studies, such as is proposed, for example, through DE 103 40 800 A1 or FR 2 821 751 A1.

It is a disadvantage of spacers of this type that the antibiotics-containing spacers with the zirconium oxide powder are subject to wear and tear on the sliding surfaces. This is disadvantageous in that the sliding surfaces can be impacted adversely upon exposure to a mechanical load. Abrasion can therefore occur, in particular in articulating spacers, in which the sliding surfaces of the spacers roll off on each other. Said abrasion can lead to inflammation which has a detrimental effect on the healing process.

Accordingly, it is the object of the invention to overcome the disadvantages of the prior art. In particular, a spacer according to the invention and a method according to the invention for producing the spacer should provide an easy way of preventing abrasion and of easily producing an articulation surface that is as level, stable, and robust as possible and enables the spacer thus generated to move easily without worsening the mobility of the joint, which would impair healing or cause the patient pain due to abrasion at the articulating sliding surfaces of the spacer. The device and the method should be applicable as universally as possible.

The objects of the invention are solved by an articulating joint spacer for temporary replacement of a joint, whereby the joint spacer comprises two spacer parts, which each comprise one sliding surface on which the spacer parts, in the patient-inserted state, touch against each other in mobile manner and roll off on each other, and the remaining spacer parts are made, at least in part, of a second bone cement that contains at least one water-soluble antibiotic.

The two bone cements preferably are polymethylmethacrylate bone cements.

In this context, the invention can provide the first bone cement to be arranged on the second bone cement in the region of the sliding surfaces while having a thickness of at least 1 mm, preferably to be arranged while having a thickness between 2 mm and 15 mm, particularly preferably to be arranged while having a thickness between 6 and 11 mm.

These thickness values are sufficient to provide for good stability of the sliding surfaces formed by the first bone cement.

Moreover, the invention can provide the first bone cement to comprise at least one anchoring that extends from the direction of the sliding surface conically into the remaining spacer parts, in particular into the second bone cement.

This attains a more stable connection of the two bone cements. Moreover, the amount of the expensive antibiotics-containing cement can thus be reduced.

A refinement of the invention proposes the remaining spacer parts to fully consist of the second bone cement and at least the connections of the joint spacer to the bone of the patient to consist of the second bone cement, preferably the regions of the joint heads of the joint spacer situated at a distance from the sliding surface to also consist of the second bone cement, particularly preferably the regions of the joint heads of the joint spacer situated at a distance of at least 1 mm from the sliding surface to consist of the second bone cement.

This ensures that the structure of the joint spacer is particularly simple. Moreover, it allows the largest possible parts of the surface that do not belong to the claimed sliding surface of the spacer parts to be utilised for the release of antibiotics.

The antibiotic in the second bone cement is preferably selected from the groups of aminoglycoside antibiotics, glycopeptide antibiotics, lincosamide antibiotics, quinolone antibiotics, oxazolidone antibiotics, gyrase inhibitors, carbapenemes, cyclic lipopeptides, glycylcyclines, and peptide antibiotics.

According to a particularly preferred embodiment, the antibiotic is a member selected from the group consisting of gentamicin, tobramycin, amikacin, vancomycin, teicoplanin, dalbavancin, lincosamine, clindamycin, moxifloxacin, levofloxacin, ofloxacin, ciprofloxacin, doripenem, meropenem, tigecycline, linezolide, eperezolide, ramoplanin, metronidazole, tinidazole, omidazole, and colistin, as well as salts and esters thereof.

Accordingly, the at least one antibiotic can be selected from the group consisting of gentamicin sulfate, gentamicin hydrochloride, amikacin sulfate, amikacin hydrochloride, tobramycin sulfate, tobramycin hydrochloride, clindamycin hydrochloride, lincosamine hydrochloride, and moxifloxacin.

It is particularly preferred, according to the invention, for the low-abrasion first bone cement to contain a radiopaque powder with a Mohs hardness of less than 8, preferably a Mohs hardness of less than 6, particularly preferably a Mohs hardness of less than 4.

The lower the hardness of the radiopaque powder of the first bone cement, the less of a contribution is made to the abrasion of the sliding surfaces.

Particularly preferably, the invention can provide the hardness of the radiopaque powder in the first bone cement to be matched to the hardness of the remaining first bone cement, preferably the difference in the Mohs hardness of the components to be less than 2, particularly preferably to be less than 1. Matching the hardness of the radiopaque powder to the hardness of the other solid component or other solid components, the abrasion of the sliding surfaces is reduced markedly.

The invention can just as well provide the second bone cement to contain a mixture of at least two antibiotics, preferably selected from gentamicin, vancomycin, and clindamycin.

Mixtures of this type are particularly well-suited for treatment of joint infections.

Moreover, the invention can provide the inside of the spacer parts to consist of the first bone cement.

As a result, the quantity of second bone cement used can be reduced, which not only saves costs, but also foregoes the unnecessary use of antibiotics.

A particularly preferred refinement of the invention proposes the free surface of the first bone cement to be coated by at least one antibiotic.

By this means, this surface can also contribute to infection control right after insertion.

According to a preferred refinement, the invention can provide the low-abrasion first bone cement to contain a calcium carbonate powder and/or barium carbonate powder.

The calcium carbonate powder and the barium carbonate powder comprise, firstly, the desired radiopaque properties such that the spacer generates the desired contrast in X-ray imaging. Secondly, the hardness of said powders is lower than that of zirconium oxide powders such that the abrasion at the sliding surfaces is reduced.

The invention can just as well provide the free surface of the first bone cement to be coated by at least one antibiotic.

Particularly preferably, the invention provides the two-part joint spacer to be an articulating knee spacer.

The objects of the invention are also solved by a set for build-up of an articulating spacer of this type, comprising a cartridge and/or an application system containing the pasty low-abrasion first bone cement, or comprising a second cartridge system and/or second mixing system containing the starting components for the low-abrasion first bone cement, comprising a second cartridge and/or a second application system containing the antibiotic-containing second bone cement, or comprising a cartridge system and/or mixing system containing the starting components for the antibiotic-containing second bone cement, and comprising at least two spacer moulds for producing a moulded part from the low-abrasion first bone cement, whereby the internal surfaces of the spacer moulds comprise a negative image of the sliding surfaces to be produced.

The objects of the invention can also be solved by a set for build-up of an articulating spacer of this type, comprising at least two spacer components that consist of the first bone cement and each comprise one sliding surface of the spacer, and comprising a cartridge and/or an application system containing the antibiotic-containing second bone cement or comprising a cartridge system and/or mixing system containing the starting components for the antibiotic-containing second bone cement.

Said sets are easy to use and concurrently provide the user with the opportunity of individualised treatment of the patient. For example, an individualised and particularly well-suited mixture of antibiotics for the second bone cement can be used. It is conceivable just as well to select a particularly well-fitting spacer mould from a plurality of different spacer moulds and spacer sizes, which fits particularly well with the anatomy of the patient or the treatment scenario, in particular for individualised adaptation of the infection treatment (degree of debridement evident only during the surgery).

Moreover, the objects of the invention are solved by a method for producing a two-part articulating joint spacer, in which a sliding surface is formed in both spacer parts from a low-abrasion first bone cement and at least the surfaces of the remaining spacer parts, at least 50% thereof, are formed with a second bone cement that contains at least one water-soluble antibiotic.

The invention can preferably provide the second bone cement to be produced such as to contain an antibiotic or a mixture of different antibiotics, preferably selected from gentamicin, vancomycin, and clindamycin.

Mixtures of this type are particularly well-suited for treatment of joint infections.

A refinement of the method according to the invention proposes a radiopaque powder with a Mohs hardness of less than 8, preferably with a Mohs hardness of less than 6, particularly preferably with a Mohs hardness of less than 4, in particular calcium carbonate powder and/or barium carbonate powder, to be admixed to the first bone cement.

The lower the hardness of the radiopaque powder of the first bone cement, the less of a contribution is made to the abrasion of the sliding surfaces.

A preferred refinement of the method proposes to first form the second bone cement and then to apply the first bone cement onto the second bone cement and to form the sliding surfaces.

Alternatively, the invention can provide the first bone cement to be filled into a spacer mould first, whereby the sliding surface is formed by a negative image of the inside of the spacer mould, and then the second bone cement to be applied onto the first bone cement and the remaining surface of the spacer parts to be formed. In this context, the invention can preferably provide the remaining surface of the spacer parts to be formed through a negative mould of the spacer mould. Alternatively or in addition, the invention can further provide the cured spacer parts to be attached to the bone by means of the second bone cement.

Said methods are well-suited for easy implementation in the often hectic setting of a surgical theatre.

The invention is based on the surprising finding that the utilisation of two bone cements allows to generate a more stable running surface and/or sliding surface of the articulating spacer parts without foregoing the advantages of an antibiotic-releasing spacer. The spacer thus produced leads to fewer problems during its use.

Exemplary embodiments of the invention shall be illustrated in the following on the basis of one schematic FIGURE, though without limiting the scope of the invention.

FIG. 1 shows a schematic cross-sectional view of a spacer according to the invention fabricated from two bone cements (6, 7, 12, 13). The spacer shown is a two-part articulating knee spacer intended for temporary replacement of a knee joint. The selected sectional plane shown is a plane of the artificial knee joint that is parallel to the sagittal plane.

The two parts of the knee spacer are a tibial part 1 (on the bottom in FIG. 1) and a femoral part 2 (on the top in FIG. 2). The tibial part 1 is attached to a tibial bone 4 of a patient. The tibial part 1 comprises an articular head with an articular socket. The articular head is fabricated from a first bone cement 6 possessing sufficient hardness to prevent abrasion through the use of barium carbonate powder and/or calcium carbonate powder as radiopaquer and—optionally—can contain antibiotics/be antibiotics-containing. This renders the first bone cement 6 a low-abrasion bone cement. The remaining tibial part 1 is fabricated from a second bone cement 7 that contains a mixture of two water-soluble antibiotics that are matched to the manifest treatment setting of the patient.

The articular head is anchored in the tibial bone 4 by means of a conical peg 8. This attains a stable connection of the tibial part 1 to the bone 4 and reduces the quantity of antibiotic-containing bone cement 7 used in the process and thus saves antibiotics. Besides, further anchorings 8 made of the second bone cement 7 are anchored in matching conical recesses in the tibial bone 4 in order to attain a more stable connection of the tibial part 1 of the spacer to the tibial bone 4.

The femoral part 2 of the spacer is structured alike. An articular head is formed on the femoral bone 10 of a patient from a low-abrasion bone cement 12 and attached by means of an antibiotics-containing bone cement 13. The first bone cement 12 of the femoral part 2 of the spacer is preferably the same as the first bone cement 6 of the tibial part 1 and the second bone cement 13 of the femoral part 2 of the spacer is preferably the same as the second bone cement 7 of the tibial part 1 of the spacer. A stable connection of the articular head to the femoral bone 10 is attained by means of a conical anchoring 14.

With the exception of the articular heads, the surfaces of the two spacer parts 1, 2 are implemented by means of the second bone cement 7, 13 and can therefore release antibiotics in the patient-inserted state, in particular in the direction of the bones 4, 10 of the patient.

In the state intended, i.e. in the patient-inserted state shown in FIG. 1, the two spacer parts 1, 2 touch against each other by means of the articular heads. For this purpose, similar to a natural knee joint, sliding surfaces 16, 18 are provided at the surfaces of the articular heads by means of which the two spacer parts 1, 2 can roll off on each other and/or slide over each other.

As a result, articulation of the spacer parts 1, 2 and thus replication of the functional mechanism of the knee is feasible.

Since the sliding surfaces 16, 18 are fabricated from the low-abrasion first bone cement 6, 12, the sliding surfaces 16, 18 remain intact during the dwell time of the temporary knee spacer such that no (or only very few) particles detach from the sliding surfaces 16, 18. As a result, the mobility of the knee spacer is kept intact and there is no adverse abrasion effect on the healing process.

Concurrently, the mixture of antibiotics is continually eluted by dissolution out of the second bone cement 7, 13 of the two spacer parts 1, 2 in order to support healing and is thus available for infection control.

The example shown relates to a knee spacer that is preferred according to the invention. However, the invention is not limited to knee spacers, but also relates to any other form of two-part temporary joint spacers, such as, for example, elbow spacers, hip spacers, ankle spacers or shoulder spacers. It is obvious to a person skilled in the art to apply the example described by means of FIG. 1 to spacers for other joints.

The features of the invention disclosed in the preceding description and in the claims, figures, and exemplary embodiments, can be essential for the implementation of the various embodiments of the invention both alone and in any combination.

LIST OF REFERENCE NUMBERS

1 Spacer part/tibial part
2 Spacer part/femoral part
4 Bone (tibia)
6 Low-abrasion bone cement (tibial part)
7 Antibiotics-containing cement (tibial part)
8 Anchoring
10 Bone (femur)
12 Low-abrasion bone cement (femoral part)
13 Antibiotics-containing cement (femoral part)
14 Anchoring
16 surface (tibial part)
18 Sliding surface (femoral part)

The invention claimed is:

1. An articulating joint spacer for temporary replacement of a joint comprising two spacer parts,
   wherein each of the two spacer parts comprises
      (1) a first portion comprising a first layer,
         which first layer comprises a first bone cement which is a low-abrasion bone cement, and a sliding surface,
         the sliding surfaces of the two spacer parts being configured to touch against each other in a mobile manner and roll off on each other in a patient-inserted state, and
      (2) a remaining portion comprising a second layer,
         which second layer comprises a second non low abrasion bone cement that contains at least one water-soluble antibiotic,
      wherein the first bone cement and the second bone cement comprise different bone cement materials.

2. The articulating joint spacer according to claim 1, wherein the first layer has a thickness of at least 1 mm and is arranged directly on the second layer.

3. The articulating joint spacer according to claim 2, wherein the first layer has a thickness between 6 and 11 mm.

4. The articulating joint spacer according to claim 1, wherein the first layer comprises at least one anchoring component that extends from a direction of the sliding surface conically into the remaining portion and/or into the second layer.

5. The articulating joint spacer according to claim 1 wherein the remaining portion consists of the second bone cement, and connections of the spacer parts to a patient's bone consist of the second bone cement, and a region of the spacer parts located at a distance from the sliding surface consists of the second bone cement.

6. The articulating joint spacer according to claim 5 wherein the region of the spacer parts is situated at a distance of at least 1 mm from the sliding surface.

7. The articulating joint spacer according to claim 1 wherein the first bone cement comprises a radiopaque powder with a Mohs hardness of less than 8.

8. The articulating joint spacer according to claim 7 wherein the first bone cement comprises a radiopaque powder with a Mohs hardness of less than 4.

9. The articulating joint spacer according to claim 1 wherein the second bone cement comprises a mixture of at least two antibiotics selected from the group consisting of gentamicin, vancomycin, and clindamycin.

10. The articulating joint spacer according to claim 1 wherein a free surface of the first layer is coated by at least one antibiotic.

11. The articulating joint spacer according to claim 1 wherein the first bone cement comprises a calcium carbonate powder and/or barium carbonate powder.

12. A kit for forming an articulating spacer according to claim 1, comprising
    (1) a cartridge and/or an application system comprising the first bone cement in a pasty form, or starting components for forming the first bone cement, and
    (2) a second cartridge and/or a second application system comprising the second bone cement, or starting components for forming the second bone cement, and
    (3) at least two spacer moulds for producing a moulded part from the first bone cement, whereby internal surfaces of the at least two spacer moulds comprise a negative image of the sliding surfaces to be produced.

13. A kit for forming an articulating spacer according to claim 1, comprising
    (1) at least two spacer components formed from a material which consists of the first bone cement, each of said at least two spacer components comprising one sliding surface, and
    (2) a cartridge and/or an application system comprising the second bone cement or starting components for forming the second bone cement.

14. The articulating joint spacer according to claim 1 consisting of the first portion and the remaining portion.

15. The articulating joint spacer according to claim 1, wherein the two spacer parts touch only at the sliding surfaces.

* * * * *